(12) United States Patent
Sekiya et al.

(10) Patent No.: US 8,671,740 B2
(45) Date of Patent: Mar. 18, 2014

(54) GAS CONCENTRATION DETECTION SENSOR

(75) Inventors: Takayuki Sekiya, Nissin (JP); Kei Kosaka, Nagoya (JP); Shodai Hirata, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 124 days.

(21) Appl. No.: 13/109,374

(22) Filed: May 17, 2011

(65) Prior Publication Data

US 2011/0283774 A1     Nov. 24, 2011

(30) Foreign Application Priority Data

May 18, 2010   (JP) .................................. 2010-113861

(51) Int. Cl.
  *G01N 27/00*     (2006.01)
(52) U.S. Cl.
  USPC .......................... 73/31.05; 73/23.31; 204/428
(58) Field of Classification Search
  USPC .......... 73/23.2, 31.05, 114.71, 114.73, 23.31, 73/30.01, 23.4, 24.06, 25.05, 29.05, 73/30.04; 204/428
  See application file for complete search history.

(56) References Cited

U.S. PATENT DOCUMENTS

| | | | |
|---|---|---|---|
| 6,279,376 B1 | 8/2001 | Yamada et al. | |
| 2003/0019280 A1 | 1/2003 | Toguchi et al. | |
| 2005/0016257 A1 | 1/2005 | Isomura et al. | |
| 2005/0029101 A1 | 2/2005 | Isomura et al. | |
| 2005/0198810 A1 | 9/2005 | Taguchi et al. | |
| 2008/0236248 A1* | 10/2008 | Ikoma et al. | 73/23.31 |

FOREIGN PATENT DOCUMENTS

| | | |
|---|---|---|
| EP | 1 046 906 A2 | 10/2000 |
| JP | 2000-304719 | 11/2000 |
| JP | 2003-107033 A1 | 4/2003 |
| JP | 3531859 B2 | 5/2004 |
| JP | 2005-043349 A1 | 2/2005 |
| JP | 2005-292119 A1 | 10/2005 |
| JP | 4355622 B2 | 11/2009 |
| JP | 4461185 B2 | 5/2010 |

* cited by examiner

*Primary Examiner* — Daniel S Larkin
*Assistant Examiner* — Jamar Ray
(74) *Attorney, Agent, or Firm* — Burr & Brown, PLLC

(57) ABSTRACT

The sensor element, which can detect the concentration of a specified gas, is held with a housing with a front end thereof exposed. A protective cover includes an inner cover and an outer cover, and secured to the housing. A ratio φ1/φ2 is set to a range from 0.6 to 0.9, where φ1 represents an outer diameter of a portion where an inner gas aperture is formed in the inner cover, and φ2 represents an inner diameter of a portion where an outer gas aperture is formed in the outer cover.

4 Claims, 9 Drawing Sheets

GAS CONCENTRATION DETECTION SENSOR

BACKGROUND OF THE INVENTION

1. Field of the Invention

The present invention relates to gas concentration detection sensors.

2. Description of the Related Art

To date, a gas concentration detection sensor that detects the concentration of a specified gas such as NOx or oxygen included in an object gas such as an exhaust gas from an automobile has been known. In this gas concentration detection sensor, the temperature of a sensor element may be decreased and cracking may occur due to, for example, adhesion of water generated when an engine is started to the sensor element, or a sudden increase in the flow rate of the object gas that strikes the sensor element. For this reason, a technology that prevents these disadvantages by mounting a protective cover that covers the sensor element has been proposed. For example, a gas concentration detection sensor described in Patent Document 1 is provided with a double-layered protector, which has a vent hole formed therein in order to introduce an exhaust gas into the sensor, along the outer circumference of the front end of the sensor element as a protective cover.

PRIOR ART DOCUMENTS

Patent Document

[Patent Document 1] Japanese Unexamined Patent Application Publication No. 2000-304719 (FIG. 11)

SUMMARY OF THE INVENTION

However, when such a double-layered protective cover is used, the response property of sensor output is not sufficiently high when the concentration of a specified gas included in the object gas is changed. In addition, even when the protective cover has the double-layered structure, water may still flow into the protective cover, adhere to the sensor element, and cool the sensor element.

The present invention is proposed in order to solve these problems. Main objects of the present invention are to sufficiently increase the response property of the sensor output and to sufficiently prevent water from adhering to the sensor element in a gas concentration sensor having a double-layered protective cover.

The inventors have found that, in a gas concentration detection sensor having a double-layered protective cover, a ratio $\phi 1/\phi 2$, where $\phi 1$ is an outer diameter of a portion where inner gas apertures are formed in an inner cover and $\phi 2$ is an inner diameter of a portion where outer gas apertures are formed in an outer cover, significantly affects the response property of the sensor output and the amount of water striking the sensor element. This has led the inventors to complete the present invention.

A gas concentration detection sensor according to the present invention includes a sensor element that is held with a housing with a front end thereof exposed and is able to detect a concentration of a specified gas included in an object gas, a protective cover that is secured to the housing and protects the front end of the sensor element, and an inner cover that is one of components of the protective cover and covers the front end of the sensor element. The inner cover has an inner gas aperture that allows the object gas to flow therethrough.

The gas concentration detection sensor also includes an outer cover that is one of the components of the protective cover and covers the inner cover. The outer cover has an outer gas aperture that allows the object gas to flow therethrough and does not oppose the inner gas aperture.

In the gas concentration detection sensor, a ratio $\phi 1/\phi 2$ is from 0.6 to 0.9 where $\phi 1$ represents an outer diameter of a portion where the inner gas aperture is formed in the inner cover and $\phi 2$ represents an inner diameter of a portion where the outer gas aperture is formed in the outer cover.

In the gas concentration detection sensor including such a double-layered protective cover, the amount of time from a time when the concentration of the specified gas included in the object gas is changed to a time when the sensor output is changed in response to the change in the concentration of the specified gas (response time) decreases as the ratio $\phi 1/\phi 2$ is increased. However, the response time sharply increases when the ratio exceeds a certain range of values. Specifically, when the ratio $\phi 1/\phi 2$ is from 0.6 to 0.9, the response time is almost minimum (value like a peak). However, when the ratio $\phi 1/\phi 2$ is less than 0.6, the response time increases as the ratio $\phi 1/\phi 2$ is decreased, and when the ratio $\phi 1/\phi 2$ is more than 0.9, the response time sharply increases. In addition, as the ratio $\phi 1/\phi 2$ is increased, adhesion of water to the sensor element can be sufficiently prevented. Preferably, the ratio $\phi 1/\phi 2$ is from 0.67 to 0.87. In this range, the response property of the sensor output further increases and adhesion of water to the sensor element can be further prevented.

In the gas concentration detection sensor according to the present invention, it is preferable that the inner diameter $\phi 2$ of the outer cover be substantially the same as an outer diameter of the housing. The larger the inner diameter $\phi 2$ of the outer cover is, the smaller the minimum value of the response time is when the ratio $\phi 1/\phi 2$ is from 0.6 to 0.9. However, the inner diameter $\phi 2$ is generally made to be smaller than or equal to an outer diameter of the housing. Thus, it is preferable that the inner diameter $\phi 2$ be maximized in that range, that is, the inner diameter $\phi 2$ be made to be substantially the same as the outer diameter of the housing. The phrase "substantially the same as the outer diameter of the housing" includes a case where the inner diameter $\phi 2$ matches the outer diameter of the housing and a case where the inner diameter $\phi 2$ is larger or smaller than the outer diameter of the housing by the thickness of the outer cover.

In the gas concentration detection sensor according to the present invention, the inner cover may include a first body where the inner gas aperture is formed, a second body that is connected to the first body with a step provided therebetween and has a diameter smaller than a diameter of the first body, and a front end section that is connected to the second body and has a diameter smaller than the diameter of the second body. The outer cover may include a body where the outer gas aperture is formed, a front end section that is connected to the body with a step provided there between, is joined in a circumference direction to the second body of the inner cover, and has a diameter smaller than a diameter of the body. Advantages of the present invention can be effectively obtained also with the gas concentration detection sensor including the outer cover and the inner cover as above.

DETAILED DESCRIPTION OF THE INVENTION

Figure 1:
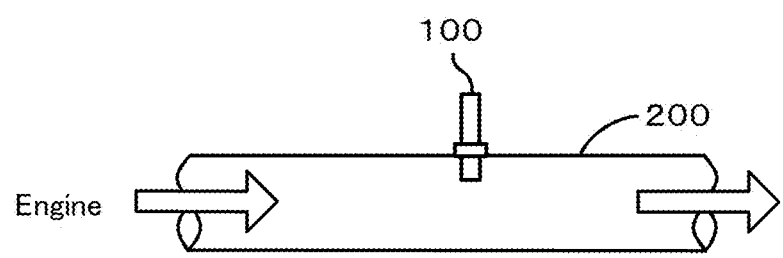
FIG. 1 is an explanatory diagrammatic view of a state in which a gas concentration detection sensor 100 is mounted in piping 200.
Figure 2:
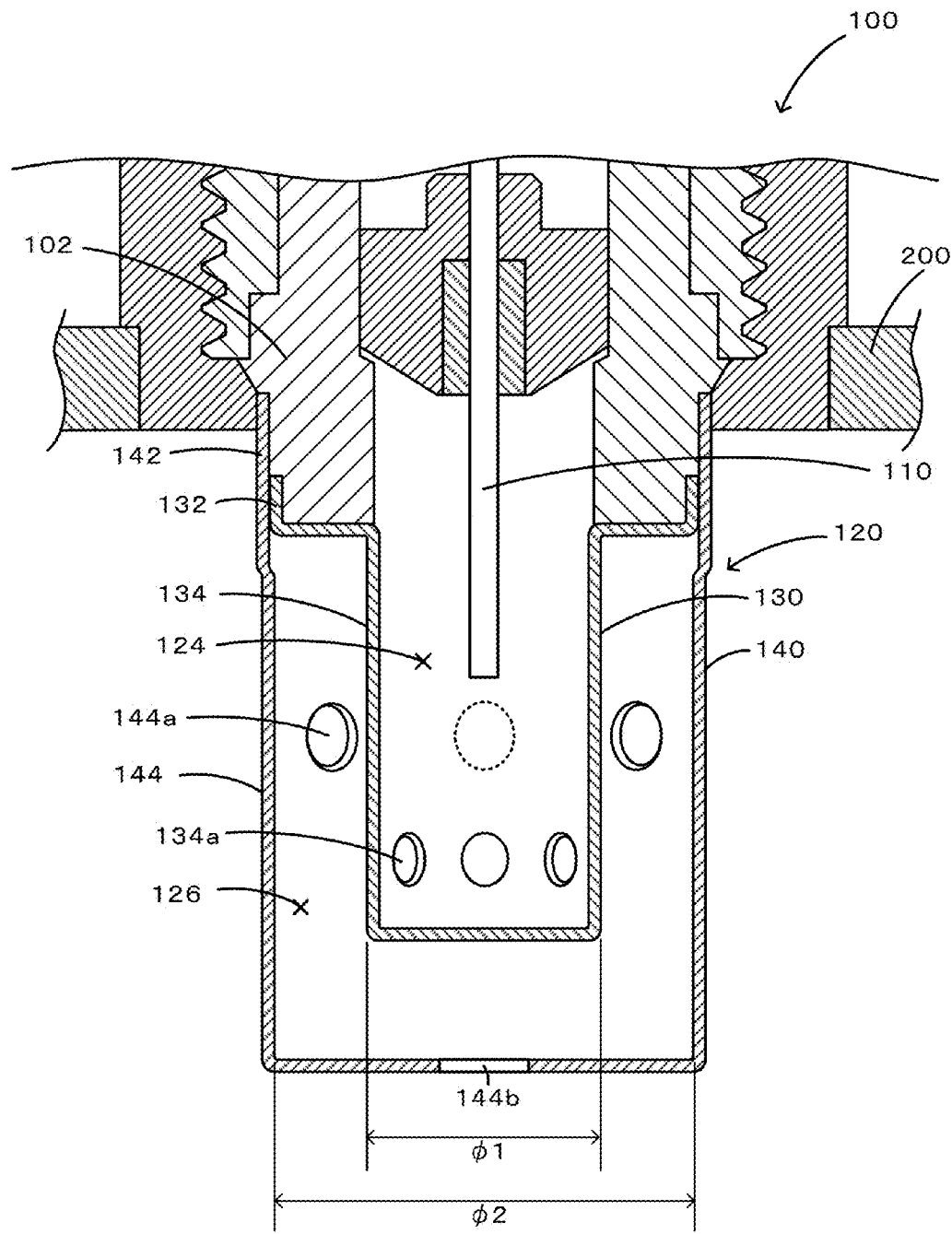
FIG. 2 is a vertical sectional view illustrating the structure of the gas concentration detection sensor 100.

Next, an embodiment according to the present invention will be described with reference to the drawings. FIG. 1 is an explanatory diagrammatic view illustrating a state in which a gas concentration detection sensor 100 is mounted in piping 200. FIG. 2 is a vertical sectional view illustrating the structure of the gas concentration detection sensor 100.

As illustrated in FIG. 1, the gas concentration detection sensor 100 is mounted in the piping 200 that extends from a vehicle engine as an exhaust path. The gas concentration detection sensor 100 is designed so as to detect the concentration of at least one of gas components such as NOx and $O_2$, included in the exhaust gas discharged from the engine as an object gas.

As illustrated in FIG. 2, the gas concentration detection sensor 100 includes a sensor element 110 having a function that detects the concentration of a gas component included in the object gas, and a protective cover 120 that protects the sensor element 110.

The sensor element 110 is a long plate-shaped element including an oxygen ion conductive solid electrolyte layer of, for example, zirconia ($ZrO_2$). The sensor element 110 is held with a housing 102 with a front end thereof exposed. The sensor element 110 includes a heater therein having a temperature control function that heats the sensor element 110 in order to keep the sensor element 110 warm. The structure of the sensor element 110 and the principle of detecting the concentration of a gas component as above are known in the art and are described in, for example, Japanese Unexamined Patent Application Publication No. 2008-164411.

The protective cover 120 is arranged so as to surround the periphery of the sensor element 110. The protective cover 120 includes an inner cover 130 that covers the front end of the sensor element 110 and an outer cover 140 that covers the inner cover 130.

The inner cover 130 is a metal (for example, stainless steel) member that includes a cylindrical large-diameter section 132 and a body 134 having a diameter smaller than that of the large-diameter section 132. The large-diameter section 132 has an inner circumferential surface that is in contact with the metal housing 102 in order to secure the inner cover 130 to the housing 102. The body 134 is a cylindrical body with a bottom having an outer diameter of $\phi 1$. The body 134 is connected to the large-diameter section 132 with a step provided therebetween and positioned so as to cover a side surface of the sensor element 110. The body 134 has equally spaced six inner gas apertures 134a formed therein in order to circulate the object gas from the outside to the inside or the inside to the outside of the inner cover 130. Each inner gas aperture 134a is a circular aperture. It is noted that $\phi 1$ represents the outer diameter of a portion where the inner gas apertures 134a are formed in the body 134. A sensor element chamber 124 that covers the front end of the sensor element 110 is formed as a space defined by the inner cover 130.

The outer cover 140 is a metal (for example, stainless steel) member that includes a cylindrical large-diameter section 142 and a body 144 having a diameter slightly smaller than that of the large-diameter section 142. The large-diameter section 142 has an inner circumferential surface that is in contact with the housing 102 and the large-diameter section 132 of the inner cover 130 in order to secure the outer cover 140 to the housing 102. The body 144 is a cylindrical body with a bottom having an inner diameter of $\phi 2(>\phi 1)$. The body 144 is connected to the large-diameter section 142 and positioned so as to cover an outer circumferential surface of the body 134 of the inner cover 130. The body 144 has equally spaced six outer gas apertures 144a formed therein in order to circulate the object gas from the outside to the inside or the inside to the outside of the outer cover 140. Each outer gas aperture 144a is a circular aperture having a diameter larger than that of the inner gas aperture 134a and formed at a position sifted upward relative to the corresponding inner gas aperture 134a. It is noted that $\phi 2$ represents the inner diameter of a portion where the outer gas apertures 144a are formed in the body 144. The body 144 has a bottom aperture 144b formed at the bottom portion thereof in order to circulate the object gas from the outside to the inside or the inside to the outside of the outer cover 140. The bottom aperture 144b is a circular aperture having a diameter larger than that of the outer gas aperture 144a and formed about the central axis of the outer cover 140. In the present embodiment, the ratio $\phi 1/\phi 2$ is designed to fall within a range from 0.6 to 0.9, and preferably within a range from 0.67 to 0.87. A diameter of a portion with which the outer cover 140 is engaged in the housing 102 is substantially almost identical to an inner diameter $\phi 2$ of the outer cover 140 (slightly larger than $\phi 2$).

A gas circulating chamber 126 is a space defined by the body 134 of the inner cover 130 and the body 144 of the outer cover 140.

Next, a flow of the object gas when the gas concentration detection sensor 100 having the above-described structure detects the concentration of a specified gas is described below. The object gas flowing in the piping 200 flows into the gas circulating chamber 126 through any of a plurality of the outer gas apertures 144a, and then flows into the sensor element chamber 124 through any of a plurality of the inner gas apertures 134a. At this time, since the outer gas apertures 144a and the inner gas apertures 134a do not oppose each other, even if the object gas contains water, most of the water flows, for example, along an outer wall of the body 134 and is discharged through the bottom aperture 144b of the outer cover 140 to the outside of the outer cover 140. Thus, it is less likely that water strikes the front end of the sensor element 110. The object gas having flowed into the sensor element chamber 124 flows back into the gas circulating chamber 126 through any of the plurality of inner gas apertures 134a and then is discharged through any of the outer gas apertures 144a to the outside of the outer cover 140.

A research by the inventors has clarified that the response property of sensor output due to a change in the concentration of the specified gas included in the object gas significantly varies in accordance with the ratio $\phi 1/\phi 2$, which is the ratio of the outer diameter $\phi 1$ of the inner cover 130 to the inner diameter $\phi 2$ of the outer cover 140. In the present embodiment, the ratio φ1/φ2 is designed to fall within the above-described range. Thus, the response property of the sensor output is sufficiently increased. The inventors estimated that, when the outer diameter φ1 of the inner cover 130 was varied while the inner diameter φ2 of the outer cover 140 was fixed, the response property of the sensor output was as follows. That is, the inventors estimated that, because the volume of the sensor element chamber 124 decreased as the outer diameter φ1 of the inner cover 130 was decreased, when the concentration of the object gas was changed, the amount of time required to entirely replace the object gas before the change with the object gas after the change in the sensor element chamber 124 decreased, and the response property increased. However, as a result of a series of experiments, it turned out that, contrary to the estimation, the response property increased as the outer diameter φ1 of the inner cover 130 was increased. Although the reason for this has not been clarified, one probable reason is as follows. That is, although the volume of the sensor element chamber 124 increases as the outer diameter φ1 of the inner cover 130 increases, this decreases the gap between the inner cover 130 and the outer cover 140. Thus, a speed at which the object gas passes through the gas circulating chamber 126 is sufficiently increased, and, as a result, replacement of the gas in the sensor element chamber 124 becomes faster. However, when the outer diameter φ1 of the inner cover 130 was excessively increased (that is, the ratio φ1/φ2 was too close to 1), the response property was sharply decreased. The probable cause of this is that, since the gap between the inner cover 130 and the outer cover 140 becomes too small, the speed of the object gas was decreased due to friction caused between the passing gas and wall surfaces. Even when the protective cover 120 has a double-layered structure, there is a possibility that the sensor element 110 may be cooled due to adhesion of water to the sensor element 110. In the present embodiment, since the ratio φ1/φ2 is designed to fall within the above-described range, striking of water on the sensor element 110 can be sufficiently prevented.

According to the present embodiment described above in detail, in the gas concentration detection sensor 100 including the double-layered protective cover 120, since the ratio φ1/φ2 is designed to fall within a range from 0.6 to 0.9, or preferably within a range from 0.67 to 0.87, the response property of the sensor output can be sufficiently increased and adhesion of water to the sensor element 110 can be sufficiently prevented.

The present invention is not limited to the above-described embodiment. It is clear that the present invention can be implemented in a variety of embodiments without departing from the technical scope thereof.

Figure 3:
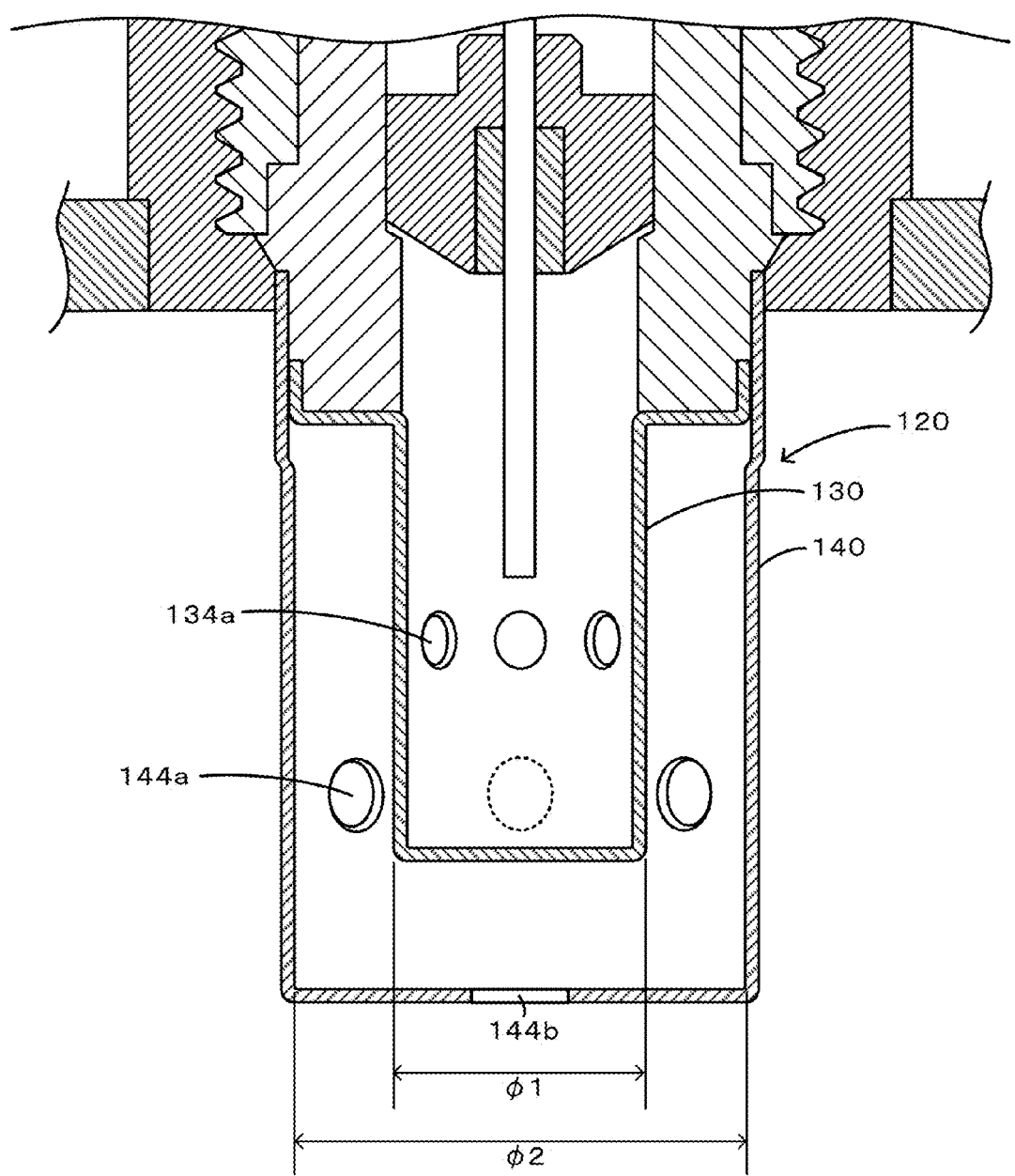
FIG. 3 is a vertical sectional view illustrating the structure of another gas concentration detection sensor.

For example, in the above-described embodiment, the outer gas apertures 144a of the outer cover 140 are disposed upper to the inner gas apertures 134a of the inner cover 130. However, as illustrated in FIG. 3, the outer gas apertures 144a of the outer cover 140 may be disposed lower to the inner gas apertures 134a of the inner cover 130. Also in this case, when the ratio φ1/φ2 is designed to fall within the above-described range, advantages similar to the above-described embodiment can be obtained.

Figure 4:
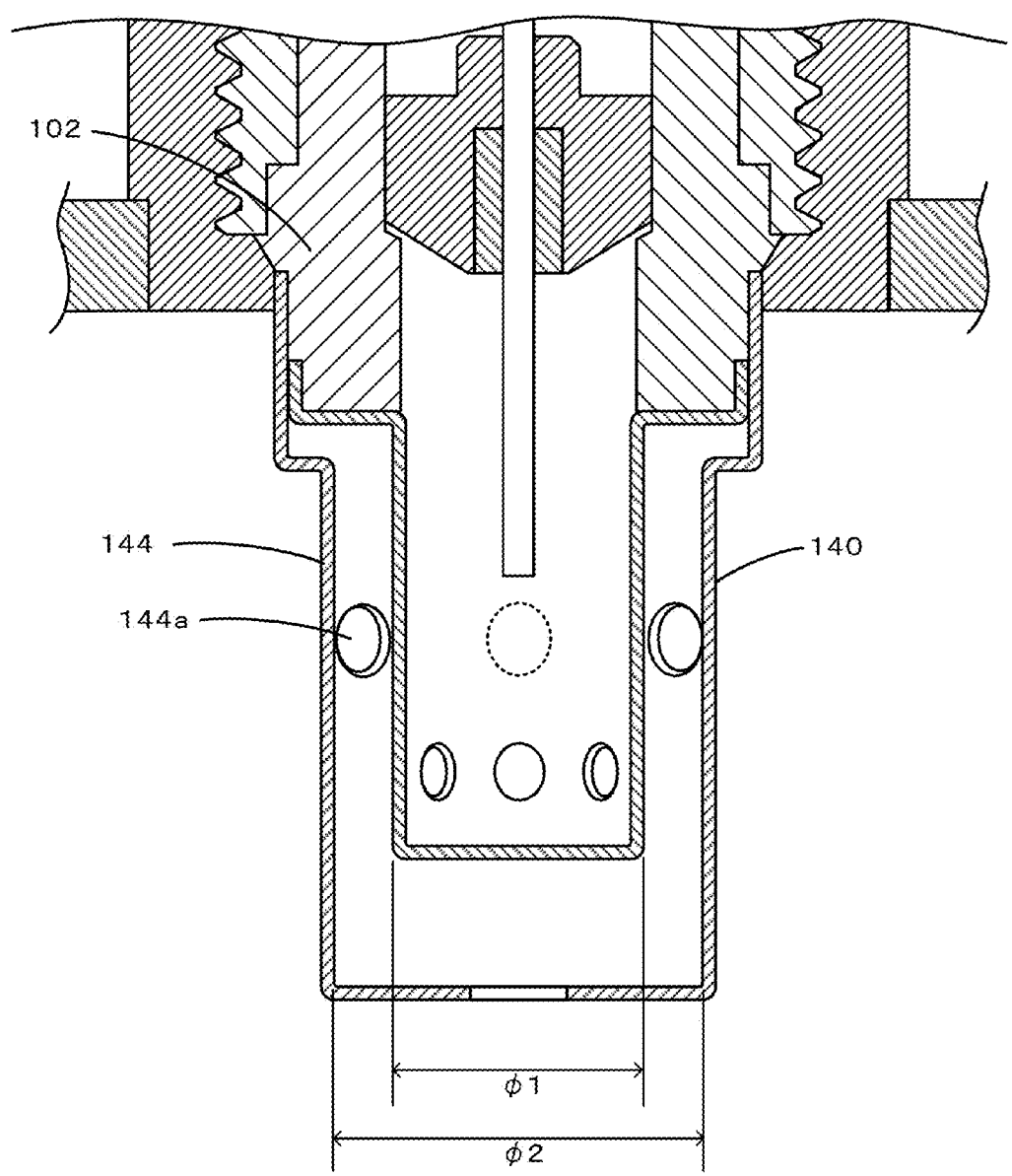
FIG. 4 is a vertical sectional view illustrating the structure of another gas concentration detection sensor.

In the above-described embodiment, out of the body 144 of the outer cover 140, the inner diameter φ2 of the portion where the outer gas apertures 144a are formed in the body 144 is made to be almost equal to the diameter of the portion with which the outer cover 140 is engaged in the housing 102. However, as illustrated in FIG. 4, the inner diameter φ2 may be made to be smaller than the diameter of the portion with which the outer cover 140 is engaged in the housing 102. Also in this case, when the ratio φ1/φ2 is designed to fall within the above-described range, advantages similar to the above-described embodiment can be obtained. However, when the ratio φ1/φ2 is the same value, the structure illustrated in FIG. 2 exhibits the response property of the sensor output higher than that which the structures illustrated in FIG. 4 exhibits. Thus, it is preferable that the inner diameter φ2 be substantially the same as the outer diameter of the housing 102.

Figure 5:
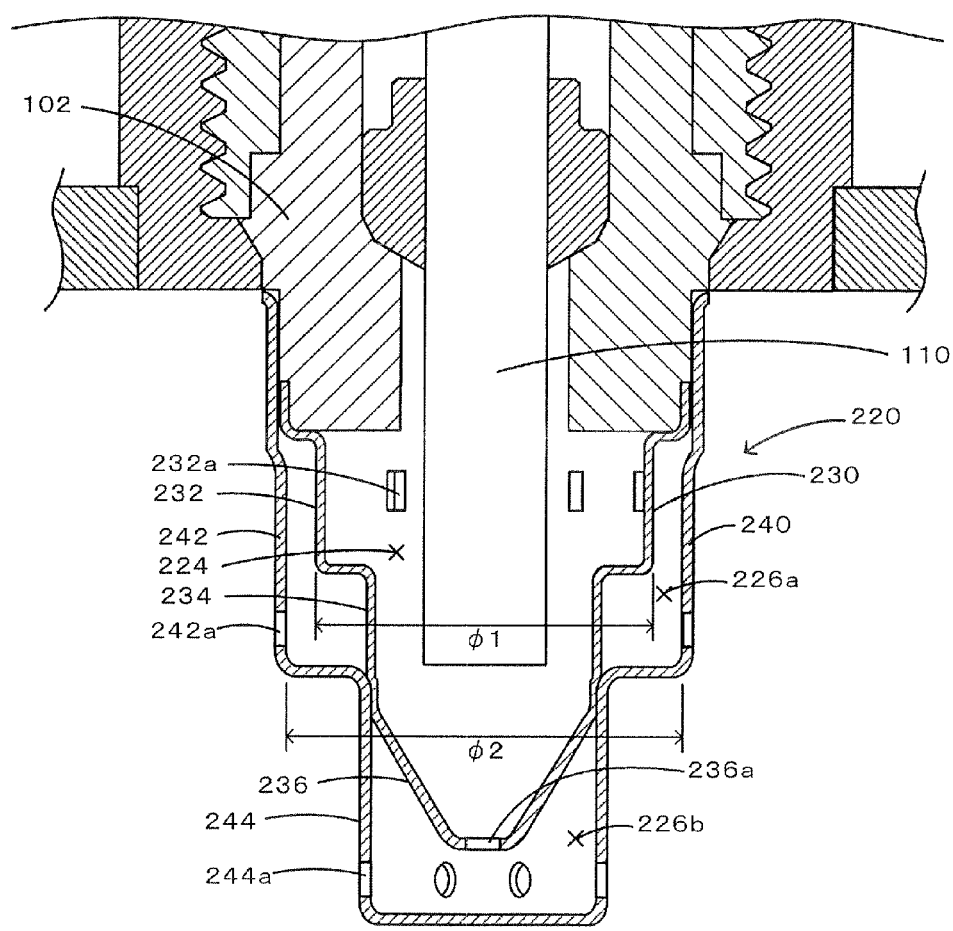
FIG. 5 is a vertical sectional view illustrating the structure of another gas concentration detection sensor.

Instead of the double-layered protective cover 120 of the above-described embodiment, a protective cover 220 illustrated in FIG. 5 may be used. That is, the protective cover 220 includes an inner cover 230 and an outer cover 240. The inner cover 230 includes a first body 232, a second body 234, and a front end section 236. Out of these sections, the first body 232 is a cylindrical body having an outer diameter of φ1 and has inner gas apertures 232a formed therein. The second body 234 is a cylindrical body that has a diameter smaller than that of the first body 232 and is connected to the first body 232 with a step provided therebetween. The front end section 236 is formed to have a reverse truncated triangular pyramid shape and is connected to the second body 234. In a lower end surface of the front end section 236, a bottom aperture 236a is formed. The outer cover 240 includes a body 242 and a front end section 244. Out of these sections, the body 242 is a cylindrical body having an inner diameter φ2 and has outer gas apertures 242a formed therein. The outer gas apertures 242a and the inner gas apertures 232a are disposed at positions vertically shifted from each other, and do not oppose each other. The front end section 244 is a cylindrical body with a bottom that has outer gas apertures 244a formed therein and is connected to the body 242 with a step provided therebetween. An upper portion of the front end section 244 is joined to a lower portion of the second body 234. As a result, a space defined by the inner cover 230 and the outer cover 240 is divided into an upper chamber 226a and a lower chamber 226b. The object gas normally flows through the outer gas apertures 242a, the upper chamber 226a, and the inner gas apertures 232a into a sensor element chamber 224. The object gas then flows through the bottom aperture 236a and the lower chamber 226b, and is discharged through the outer gas apertures 244a to the outside of the outer cover 240. Also with the protective cover 220 as above, when the ratio φ1/φ2 is designed to fall within the above-described range, advantages similar to the above-described embodiment can be obtained.

In the above-described embodiment, the numbers of the inner gas apertures 134a and the outer gas apertures 144a are not particularly limited to six. For example, the numbers may be set in a range from three to ten. When the orientation of the gas concentration detection sensor 100 can be determined, the numbers may be two.

EXAMPLES

Experimental Examples 1 to 10, 11 to 16

A plurality of the gas concentration detection sensors 100 illustrated in FIG. 2 were fabricated. Specifically, the housing 102 used had the following dimensions. That is, an outer diameter of a portion with which the inner cover 130 was engaged in the housing 102 was 12.9 mm, and the outer diameter of the portion with which the outer cover 140 was engaged in the housing 102 was 14.3 mm. The inner cover 130 used had the following dimensions. That is, the board thickness was 0.3 mm, the length of the body 134 was 12.4 mm, and a diameter of each inner gas aperture 134a was 1.5 mm. The outer cover 140 used had the following dimensions. That is, the board thickness was 0.4 mm, the length of the body 144 was 15 mm, the inner diameter φ2 of the body 144 was 13.8 mm, and the diameter of each outer gas aperture 144*a* was 2 mm. The outer diameters φ1 of the bodies 134 of the inner covers 130 were varied among experimental examples as described for experimental examples 1 to 10 in Table 1. The gas concentration detection sensor 100 fabricated here was made to detect the concentration of oxygen.

The following response property of the sensor output and the amount of water striking the front end of the sensor were observed for each gas concentration detection sensor 100. The results are listed in Table 1 and illustrated in FIGS. 7 and 8. Methods of testing the response property of the sensor output and the amount of water striking the sensor element are as follows.

—Response Property of Sensor Output—

Initially, each of the gas concentration detection sensor 100 was mounted in the piping 200 as illustrated in FIG. 1. In this state, burner combustion was used and a reference gas, of which NO concentration and lambda were respectively controlled to 70 ppm and 1.05, was caused to flow as the object gas instead of an exhaust gas from an engine while waiting for the sensor output to be stabilized. After that, oxygen was introduced into the reference gas through a gas introduction aperture, and a mixed gas, of which NO concentration was 70 ppm and lambda was 1.35, was caused to flow while waiting for the sensor output to be stabilized. Then, the sensor element 110 functioned as an oxygen concentration cell, an electromotive force was generated, and the sensor output rose. Here, from a time when oxygen was introduced into the reference gas, the amount of time required for the sensor output to reach 10% of a maximum rise value is represented as time t10, and the amount of time required for the sensor output to reach 90% of the maximum rise value is represented as time t90. Time t10 and t90 were measured, and the difference between these amounts of time, Δt (=t90−t10), is assumed as the response time (unit: sec). The shorter the response time is, the higher the response property of the gas concentration detection sensor 100 is.

—Amount of Water Striking Front End of Sensor—

Figure 6:
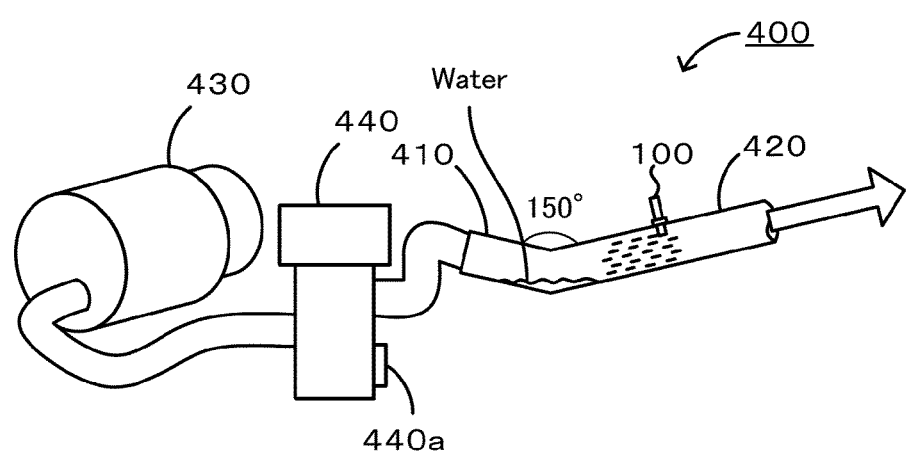
FIG. 6 is an explanatory view of a striking water amount measuring device 400.

The amount of striking water was determined using a striking water amount measuring device 400 as illustrated in FIG. 6. As the striking water amount measuring device 400, the following structure was prepared. That is, two pipes 410 and 420, each had a diameter of 28 mm, were connected to each other so as to form an angle of 150°, a blower 430 was connected at a position 300 mm away from a connection portion of the two pipes with a switching valve 440 provided therebetween, and the gas concentration detection sensor 100 was disposed at a position 400 mm away from the connection portion of the two pipes on a side opposite the blower 430. Then, with 100 ml of water retained at the connection portion of the two pipes, the blower 430 was operated under specified driving conditions in order to blow air from the blower 430 to the pipes 410 and 420. This blowing caused water retained at the connection portion of the two pipes to be blown toward the gas concentration detection sensor 100, and all the retained water was discharged to the outside of the pipe 420. During the blowing, the power of the built-in heater was controlled such that the temperature of the sensor element 110 stayed at a target value of 100° C. The power control value increases due to a decrease in the temperature when water strikes the front end of the sensor element 110. Therefore, it can be said that the larger the power control value is, the larger the amount of water striking the sensor element 110 is. The specified driving conditions of the blower 430 are as follows. That is, after the heater of the sensor element 110 is stabilized at 100° C., a flow of atmosphere at a wind speed of 75 m/s is created with the switching valve 440 connected to a bypass 440*a*, and then the switching valve 440 is switched to the pipe 410 in order to blow air to the pipe 410 for 3 seconds.

TABLE 1

| | Experimental Examples | | | | | | | | | |
|---|---|---|---|---|---|---|---|---|---|---|
| | 1 | 2 | 3 | 4 | 5 | 6 | 7 | 8 | 9 | 10 |
| Outer diameter of inner cover φ1 (mm) | 4.8 | 5.4 | 6.4 | 7.4 | 8.3 | 9.2 | 10.5 | 12 | 12.4 | 13.6 |
| Inner diameter of outer cover φ2 (mm) | | | | | 13.8 | | | | | |
| Ratio φ1/φ2 | 0.35 | 0.39 | 0.46 | 0.54 | 0.60 | 0.67 | 0.76 | 0.87 | 0.90 | 0.99 |
| Response time (sec) | 2.2 | 1.8 | 1.6 | 1.5 | 1.3 | 1.2 | 1.2 | 1.2 | 1.3 | 2 |
| Power control value | 0.25 | 0.14 | — | 0.04 | — | 0.014 | — | 0.01 | — | 0.01 |

Figure 7:
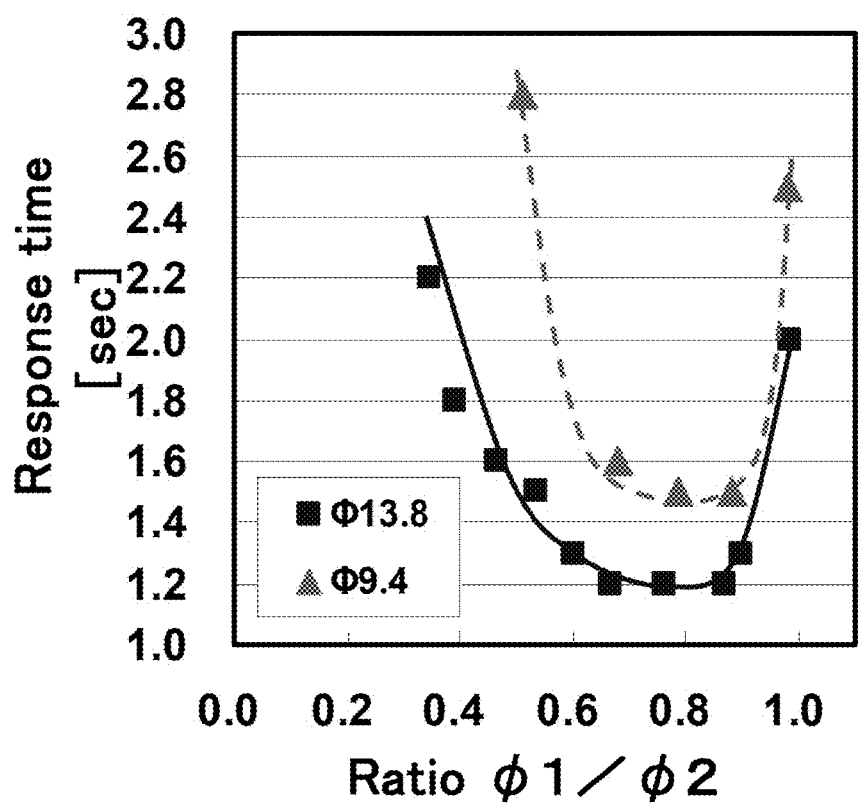
FIG. 7 is a graph illustrating the relationships between ratios $\phi 1/\phi 2$ and the response times of experimental examples 1 to 10, 11, 13 to 16.
Figure 8:
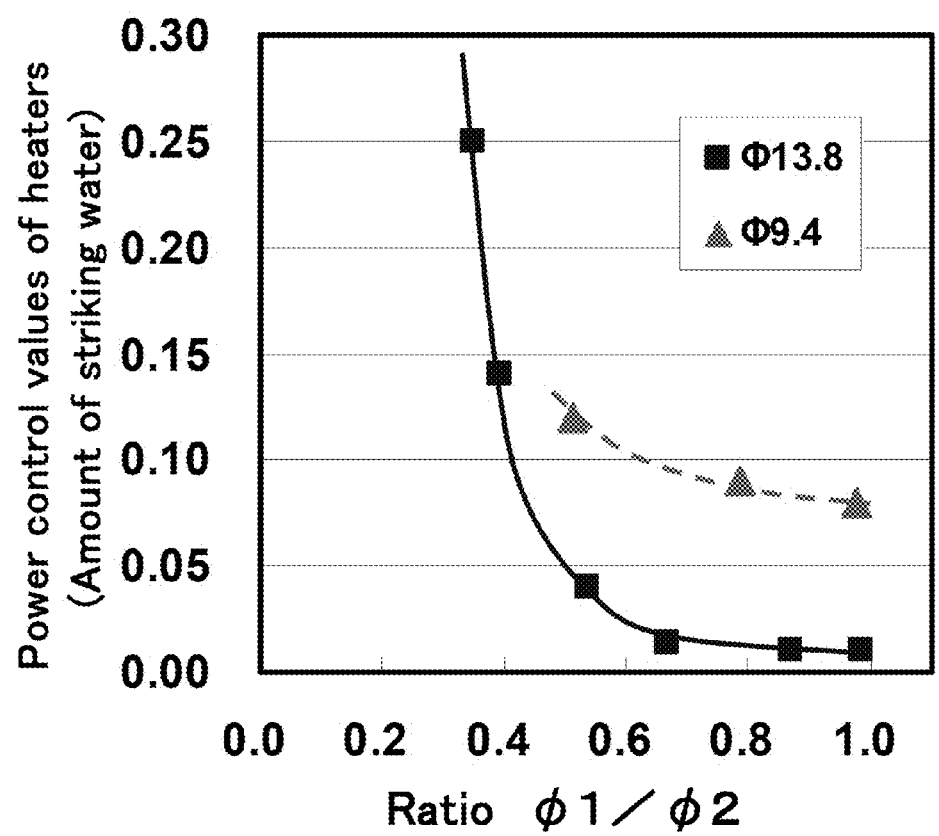
FIG. 8 is a graph illustrating the relationships between the ratios $\phi 1/\phi 2$ and power control values of heaters (amount of striking water) of experimental examples 1, 2, 4, 6, 8 and 10, 11, 14, 16

FIG. 7 is a graph illustrating the relationships between the ratios φ1/φ2 and the response times. FIG. 8 is a graph illustrating the relationships between the ratios φ1/φ2 and the power control values of the heaters (amounts of striking water). As clearly seen from Table 1 and FIG. 7, the response time significantly varied in accordance with the ratio φ1/φ2. Specifically, when the ratio φ1/φ2 was from 0.6 to 0.9, the response time was almost minimum (value like a peak). However, when the ratio φ1/φ2 was less than 0.6, the response time increased as the ratio φ1/φ2 was decreased, and when the ratio φ1/φ2 was more than 0.9, the response time sharply increased. The response time further decreased when the ratio φ1/φ2 was from 0.67 to 0.87. In addition, as clearly seen from Table 1 and FIG. 8, it was observed that the amount of striking water tended to decrease as the ratio φ1/φ2 approached 1. Thus, when the response time and the amount of striking water are considered, the ratio φ1/φ2 is preferably in a range from 0.6 to 0.9 and optimally in a range from 0.67 to 0.87. In FIG. 11 of Patent Document 1 (Japanese Unexamined Patent Application Publication No. 2000-304719), a double-layered protective cover is illustrated, which has the following structure. That is, an outer diameter of an outer cover is about 14.2 mm (an inner diameter is about 13.4 mm due to the thickness of about 0.4 mm), an outer diameter of an inner cover is about 6.6 mm, and accordingly, the ratio φ1/φ2 is about 0.49.

In addition, the gas concentration detection sensors illustrated in FIG. 4 were fabricated such that the inner diameter φ2 of the body 144 of the outer cover 140 was fixed to 9.4 mm while the outer diameter φ1 of the body 134 of the inner cover 130 were different from one another. Also with these gas concentration detection sensors, the response property of the sensor output and the amount of water striking the front end of the sensor were observed (Examples 11 to 16). The results are listed in Table 2. As is the case with experimental examples 1 to 10, the response time significantly varied in accordance with the ratio φ1/φ2 and had the similar tendency to experimental examples 10 to 10. The minimum response time was found. When the ratio φ1/φ2 was the same value, the response time decreased as the inner diameter φ2 of the outer cover 140 was increased. Thus, it can be said that the response property increases when the inner diameter φ2 is increased. As is the case with experimental examples 1 to 10, the amount of striking water tended to decrease as the ratio φ1/φ2 approached 1.

TABLE 2

| | Experimental Examples | | | | | |
|---|---|---|---|---|---|---|
| | 11 | 12 | 13 | 14 | 15 | 16 |
| Outer diameter of inner cover φ1 (mm) | 4.8 | 5.4 | 6.4 | 7.4 | 8.3 | 9.2 |
| Inner diameter of outer cover φ2 (mm) | | | | 9.4 | | |
| Ratio φ1/φ2 | 0.51 | 0.57 | 0.68 | 0.79 | 0.88 | 0.98 |
| Response time (sec) | 2.8 | — | 1.6 | 1.5 | 1.5 | 2.5 |
| Power control value | 0.12 | — | — | 0.09 | — | 0.08 |

Experimental Examples 17 to 23

A plurality of the gas concentration detection sensors illustrated in FIG. 5 were fabricated. The housing 102 used had the following dimensions. That is, an outer diameter of a portion with which the inner cover 230 is engaged in the housing 102 was 12.9 mm, and an outer diameter of the portion with which the outer cover 240 is engaged in the housing 102 was 14.3 mm. The inner cover 230 used had the following dimensions. That is, the board thickness was 0.3 mm, the length of the first body 232 is 5.2 mm, the length of the second body 234 was 3.8 mm, an outer diameter of the second body 234 was 8.2 mm, the length of the front end section 236 was 4.9 mm, a diameter of the lower end surface of the front end section 236 was 2.4 mm, the length and the width of each rectangular inner gas aperture 232a were respectively 1.5 mm and 0.3 mm, and a diameter of the bottom aperture 236a was 1 mm. The outer cover 240 used had the following dimensions. That is, the board thickness was 0.4 mm, the length of the body 242 was 7.7 mm, the inner diameter φ2 of the body 242 was 13.8 mm, the length of the front end section 244 was 9.6 mm, an inner diameter of the front end section 244 was 11.2 mm, and a diameter of each of the outer gas apertures 242a and the outer gas apertures 244a was 1 mm. The outer diameters φ1 of the inner covers 230 were varied among experimental examples as described in Table 3 for experimental examples 17 to 23. The response property of the sensor output was measured with the obtained experimental examples 17 to 23 of the gas concentration detection sensors. The results are listed in Table 3 and illustrated in FIG. 9.

TABLE 3

| | Experimental Examples | | | | | | |
|---|---|---|---|---|---|---|---|
| | 17 | 18 | 19 | 20 | 21 | 22 | 23 |
| Outer diameter of inner cover φ1 (mm) | 6 | 7.1 | 8.3 | 9.6 | 12 | 12.4 | 13.6 |
| Inner diameter of outer cover φ2 (mm) | | | | 13.8 | | | |
| Ratio φ1/φ2 | 0.43 | 0.51 | 0.60 | 0.70 | 0.87 | 0.90 | 0.99 |
| Response time (sec) | 2.4 | 1.8 | 1 | 0.7 | 0.7 | 0.75 | 1 |

Figure 9:
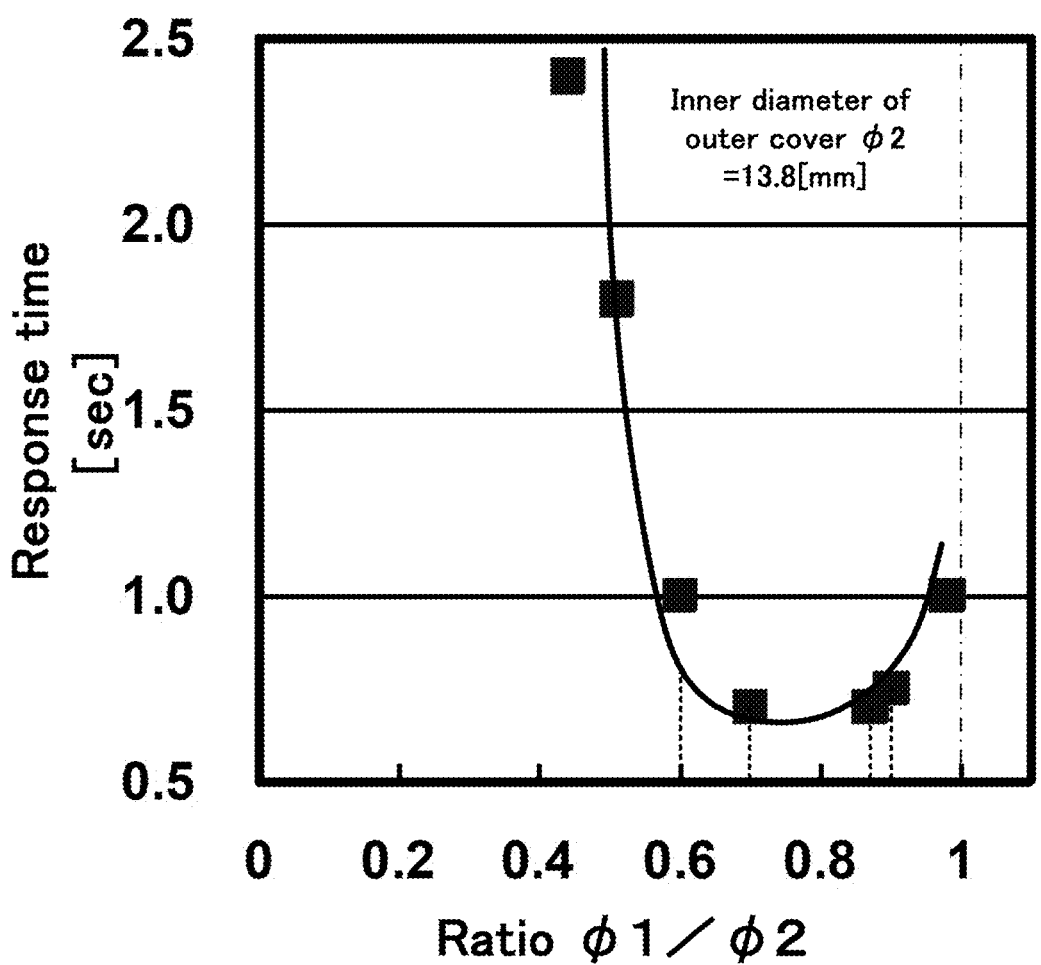
FIG. 9 is a graph illustrating the relationships between ratios $\phi 1/\phi 2$ and the response times of experimental examples 17 to 23.

As clearly seen from Table 3 and FIG. 9, as is the case with experimental examples 1 to 10, the response time significantly varied in accordance with the ratio φ1/φ2. Specifically, when the ratio φ1/φ2 was from 0.6 to 0.9, the response time was almost minimum. However, when the ratio φ1/φ2 was less than 0.6, the response time increased as the ratio φ1/φ2 was decreased, and when the ratio φ1/φ2 was more than 0.9, the response time sharply increased. The response time further decreased when the ratio φ1/φ2 was from 0.67 to 0.87. As is the case with experimental examples 1 to 10, the amount of striking water tended to decrease as the ratio φ1/φ2 approached 1.

The present application claims priority on the basis of the Japanese Patent Application No. 2010-113861 filed on May 18, 2010, the entire contents of which are incorporated herein by reference.

INDUSTRIAL APPLICABILITY

The present invention can be used as a gas concentration detection sensor that detects the concentration of a specified gas such as NOx or oxygen included in an object gas such as an exhaust gas from an automobile.

What is claimed is:

1. A gas concentration detection sensor, comprising:
   a sensor element that is held with a housing with a front end thereof exposed and is able to detect a concentration of a specified gas included in an object gas;
   a protective cover that is secured to the housing and protects the front end of the sensor element, the protective cover consisting only of an inner cover and an outer cover,
   wherein the inner cover covers and directly opposes the front end of the sensor element, and has an inner gas aperture that allows the object gas to flow therethrough,
   wherein the outer cover covers the inner cover, and has an outer gas aperture that allows the object gas to flow therethrough, the outer gas aperture not opposing the inner gas aperture,
   wherein a ratio φ1/φ2 is from 0.6 to 0.9 where φ1 represents an outer diameter of a portion where the inner gas aperture is formed in the inner cover, and φ2 represents an inner diameter of a portion where the outer gas aperture is formed in the outer cover, and wherein the inner cover includes a first body where the inner gas aperture is formed, a second body that is connected to the first body with a step provided therebetween, the second body having a diameter smaller than a diameter of the first body, and a front end section that is connected to the second body, the front end section having a diameter smaller than the diameter of the second body, wherein the outer cover includes a body where the outer gas aperture is formed, and another front end section that is connected to the body with a step provided there between, the another front end section being joined in a circumference direction to the second body of the inner cover, the another front end section having a diameter smaller than a diameter of the body.

2. The gas concentration detection sensor according to claim 1, wherein the ratio φ1/φ2 is from 0.67 to 0.87.

3. The gas concentration detection sensor according to claim 1, wherein the inner diameter φ2 of the outer cover is within ±0.4 mm of an outer diameter of the housing.

4. The gas concentration detection sensor according to claim 1, wherein an entirety of the inner cover directly opposes the outer cover.

* * * * *